(12) United States Patent
Suda et al.

(10) Patent No.: US 7,370,538 B2
(45) Date of Patent: May 13, 2008

(54) METHOD AND APPARATUS FOR DETERMINING INSULATION THICKNESS

(75) Inventors: Michael D. Suda, Warrington, PA (US); Jeffrey R. Sacks, Hatfield, PA (US)

(73) Assignee: CertainTeed Corporation, Valley Forge, PA (US)

( * ) Notice: Subject to any disclaimer, the term of this patent is extended or adjusted under 35 U.S.C. 154(b) by 125 days.

(21) Appl. No.: 11/177,544

(22) Filed: Jul. 8, 2005

(65) Prior Publication Data

US 2007/0006664 A1  Jan. 11, 2007

(51) Int. Cl.
*G01N 3/08* (2006.01)

(52) U.S. Cl. ............................. 73/818; 73/819; 73/821; 73/825; 73/862.451; 73/12.05; 73/12.06; 73/12.07

(58) Field of Classification Search ............... 73/818, 73/819, 821, 825, 862.451, 12.04, 12.05, 73/12.06, 12.07, 12.09, 12.11
See application file for complete search history.

(56) References Cited

U.S. PATENT DOCUMENTS

| | | | | |
|---|---|---|---|---|
| 3,786,676 A | * | 1/1974 | Korolyshun et al. | .......... 73/817 |
| 4,337,666 A | * | 7/1982 | Bhattacharyya et al. | ...... 73/818 |
| 4,649,740 A | * | 3/1987 | Franklin | ...................... 73/49.3 |
| 5,031,464 A | * | 7/1991 | Tholerus | ....................... 73/818 |
| 5,305,646 A | * | 4/1994 | Ashmore et al. | ............. 73/818 |
| 5,365,793 A | * | 11/1994 | Terrel et al. | ................... 73/813 |
| 5,932,811 A | * | 8/1999 | Giebner | ....................... 73/818 |
| 6,848,293 B2 | * | 2/2005 | DeRuiter et al. | .......... 73/12.13 |
| 6,925,858 B2 | * | 8/2005 | Miles et al. | .................... 73/84 |
| 7,116,428 B2 | * | 10/2006 | Sauerland et al. | .......... 356/502 |
| 7,137,285 B2 | * | 11/2006 | Stroppiana | ................. 73/12.13 |

OTHER PUBLICATIONS

Standard Test Methods for Thickness and Density of Blanket or Batt Thermal, American Society for Testing Materials, Designation: C-167-98, 4 pp., Nov. 1998.

* cited by examiner

*Primary Examiner*—Edward Lefkowitz
*Assistant Examiner*—Freddie Kirkland, III
(74) *Attorney, Agent, or Firm*—Duane Morris LLP; Steven E. Koffs

(57) ABSTRACT

A method for determining the thickness of a layer of insulation comprises the steps of: contacting a top surface of a portion of the layer of insulation, compressing the portion of the layer of insulation until a predetermined compressive load is achieved, measuring a distance through which the top surface is moved during the compressing step, and determining the thickness of the layer of insulation based on the measured distance. Apparatus is provided for performing the method.

15 Claims, 7 Drawing Sheets

METHOD AND APPARATUS FOR DETERMINING INSULATION THICKNESS

FIELD OF THE INVENTION

The present invention relates to measurement generally, and more specifically to methods and apparatus for determining thickness of insulation.

BACKGROUND

ASTM standard C167-98 specifies standard methods for measuring the thickness and density of blanket or batt thermal insulation. The standard specifies use of a depth gage such as gage 600 shown in FIG. 6. The depth gage 600 has a clear plastic disk 610 of about 76 mm (3 inches) attached near or at a top end of a pin 620 having sufficient length for the material to be measured. The disk 610 is aligned perpendicular to the pin 620. A friction device is used to fix the disk to the pin. For example, the disk 610 may have a hub 612 with a female threaded sleeve 614 to receive a set screw 616. The set screw 616 can be advanced to engage a side surface of the pin 620. The pin 620 has a sharpened point 620p.

To use the depth gage 600, the disk is placed at the top end of the pin 620, as shown. The pin 620 is pushed into and through the insulation (not shown in FIG. 6), until the pin contacts a hard surface below the insulation. The set screw 616 is then loosened, so that the disk 610 can be freely lowered relative to the pin 610, until the disk contacts the top surface of the insulation. The contact is detected visually, by looking through the clear plastic disk. The set screw 616 is then tightened, and the gage 600 is removed. The distance between the bottom surface of disk 610 and the point 620p of pin 620 is the thickness of the insulation. A graduated rule (not shown) is placed against the disk 610, parallel to the pin. The distance is measured visually, by looking at where the point 620p lies along the rule.

The precision of the measurement method described above is limited by the precision of the rule, and the accuracy of the measurement is limited by any variation in the angle from which the test person views the pin 620 and rule while taking a reading. Also, during the initial step of contacting the insulation with the disk, the weight of the disk and any force inadvertently exerted by the test person may result in compression of the insulation, further reducing the accuracy of the measurement.

An improved method and apparatus for measuring insulation depth is desired.

SUMMARY OF THE INVENTION

In some embodiments, a method for determining the thickness of a layer of insulation comprises the steps of: contacting a top surface of a portion of the layer of insulation, compressing the portion of the layer of insulation until a predetermined compressive load is achieved, measuring a distance through which the top surface is moved during the compressing step, and determining the thickness of the layer of insulation based on the measured distance.

In some embodiments, apparatus comprises: at least one sensor for contacting a top surface of a portion of the layer of insulation and compressing the portion of the layer of insulation, at least one load cell coupled to the sensor for measuring a compressive load due to compression of the portion of the layer of insulation by the sensor and outputting a signal representing the compressive load, and means for measuring a distance through which the sensor is moved during compression of the portion of the layer of insulation by the sensor.

In some embodiments, apparatus comprises: a plurality of load cells, each configured to measure a respective compressive load characteristic of a portion of a layer of insulation and output a respective signal, means responsive to the signals for determining a respective individual thickness at each of the portions of the layer of insulation, and means for determining an average thickness based on the individual thicknesses.

In some embodiments, apparatus comprises: at least one device for contacting a top surface of a portion of a layer of insulation and compressing the portion of the layer of insulation with a predetermined compressive load; and an interferometer for measuring a distance through which the contacting device is moved during compression of the portion of the layer of insulation by the contacting device.

DETAILED DESCRIPTION

Figure 1:
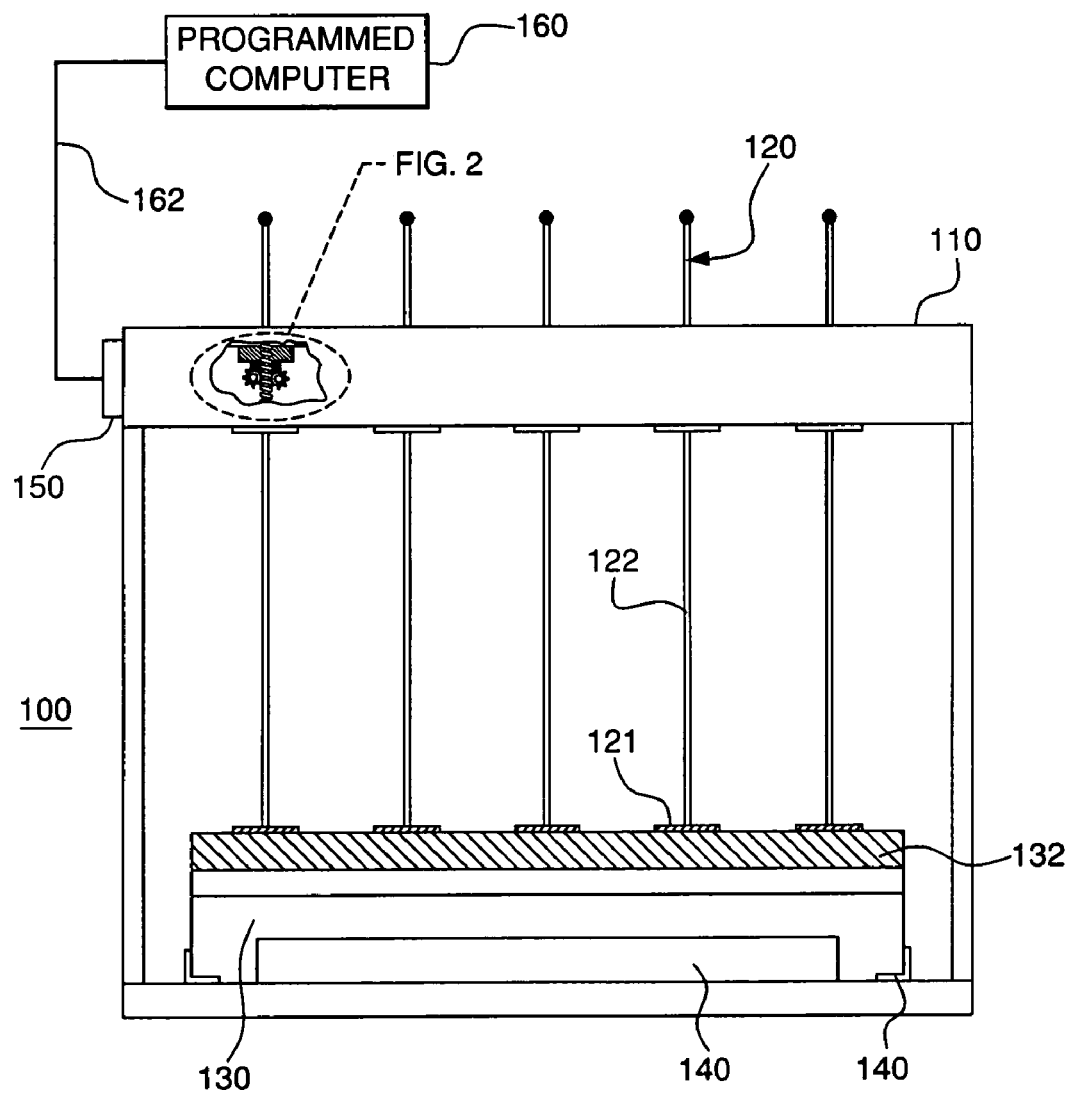
FIG. 1 is a schematic diagram of an exemplary apparatus according to one embodiment of the invention, with a partial cutaway section showing a load cell.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

FIG. 1 shows an exemplary apparatus 100 according to one embodiment. The apparatus 100 allows the application of a predetermined compressive load to the layer of insulation. The amount of compression of the insulation is measured. Given the amount of compression, the thickness of the insulation is determined, based on a predetermined relationship between the load and the resulting compression. An accurate measure of the compression can be obtained, for example, using load cell technology, eliminating the need for visual reading of thickness measurements.

Preferably, the measurement is performed non-destructively. For example, the predetermined compressive load may be selected to be about 5% to 10% of the load at which the relationship between the applied load per unit area and the percentage of thickness deformation becomes non-linear.

The apparatus 100 comprises at least one sensor 120 for contacting a top surface of a portion of the layer of insulation 132 and compressing the portion of the layer of insulation, at least one measuring means, which may be a load cell 200 (best seen in FIGS. 2A and 2B) coupled to the sensor 120 for measuring a compressive load due to compression of the portion of the layer of insulation 132 by the sensor 120 and outputting a signal 162 representing the compressive load, and a means for measuring a distance through which the sensor is moved during compression of the portion of the layer of insulation by the sensor 120.

The apparatus 100 includes a holder 140 for an insulation sample 132. The holder 140 may be a set of brackets (e.g., angle brackets) or a rectangular frame to hold a sample box 130 for loose-fill insulation 132. Other holder configurations may be used to hold other sample containers. Preferably, the holder 140 includes a plurality of movable angle brackets, to accommodate rectangular sample boxes of different sizes. Alternatively, a blanket or batt of insulation can be placed directly in the holder 140.

Figure 2A:
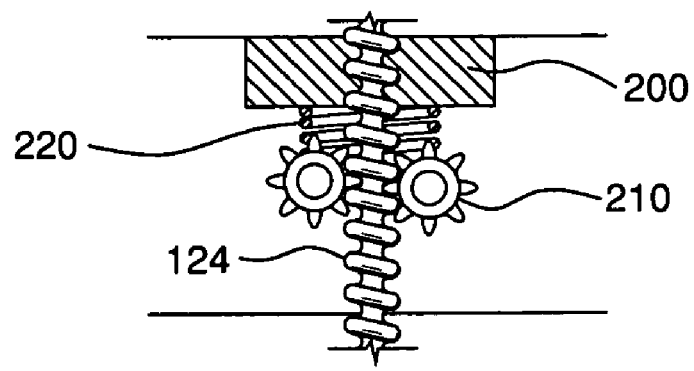
FIG. 2A is an enlarged detail of FIG. 1, showing the load cell.
Figure 3:
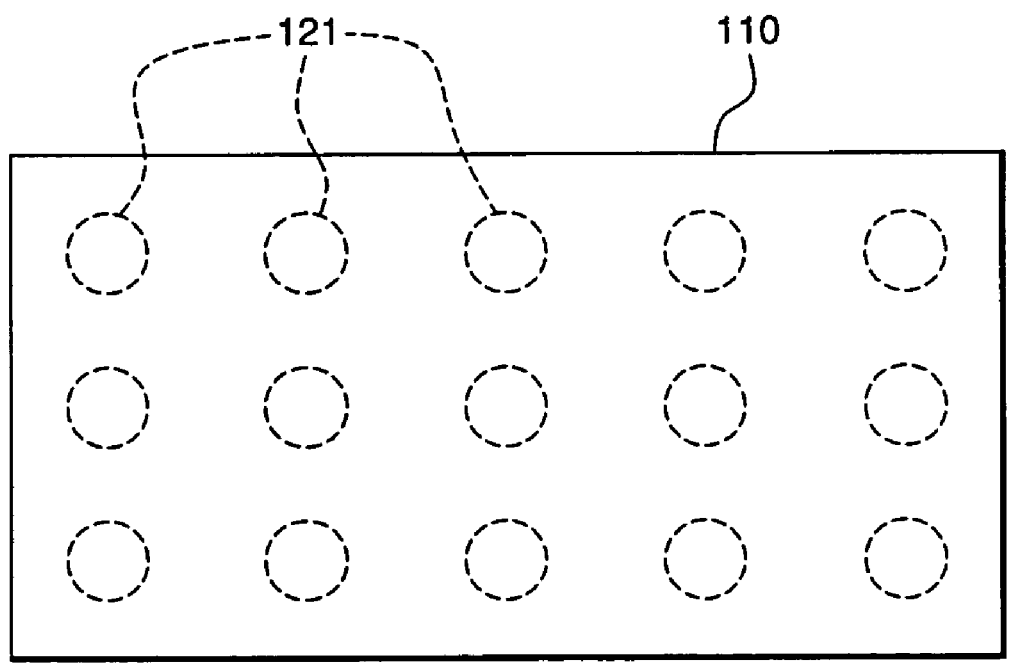
FIG. 3 is a top plan view of the apparatus of FIG. 1.
Figure 2B:
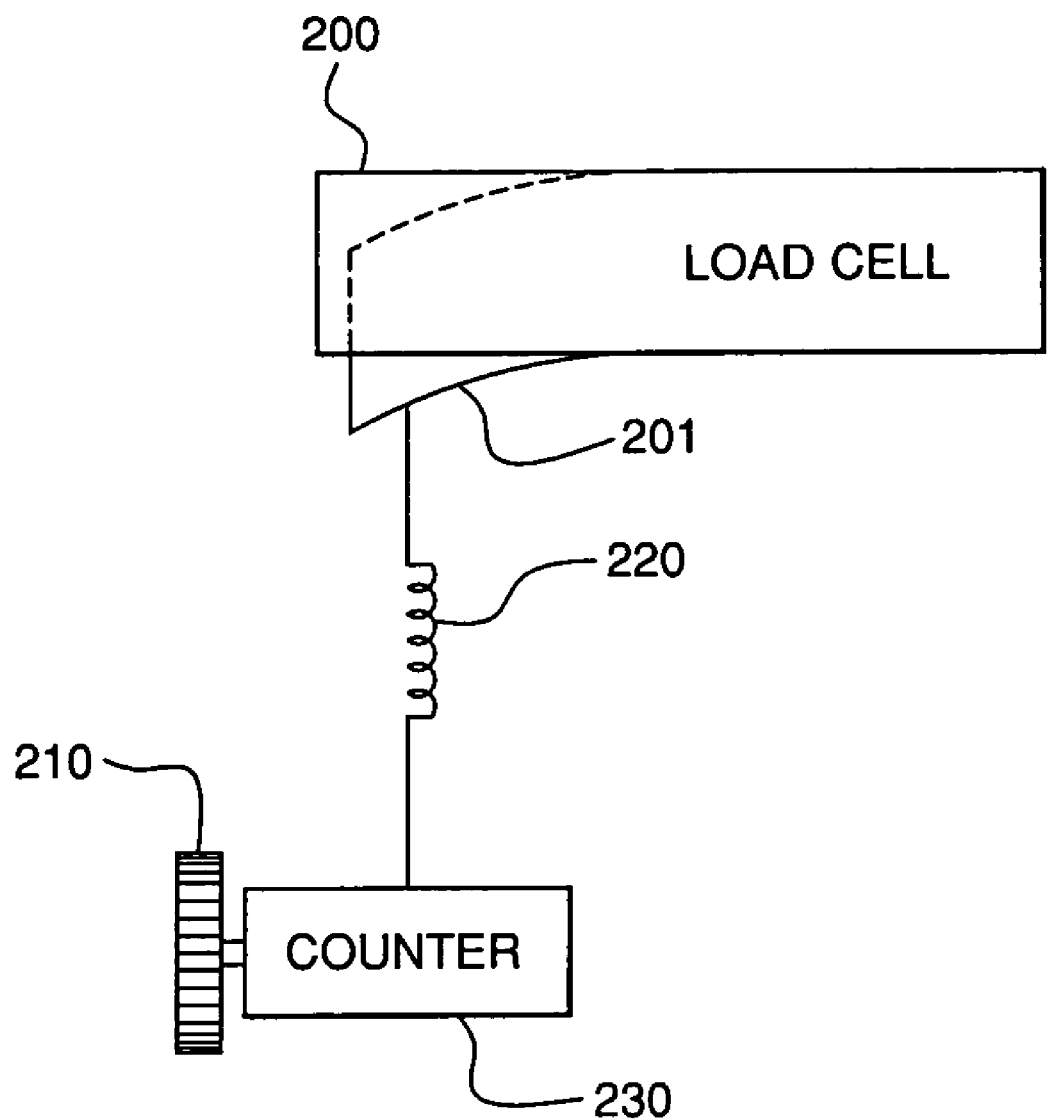
FIG. 2B is a schematic diagram of the apparatus in FIG. 2A, showing how the gears are coupled to the load cell.
Figure 4:
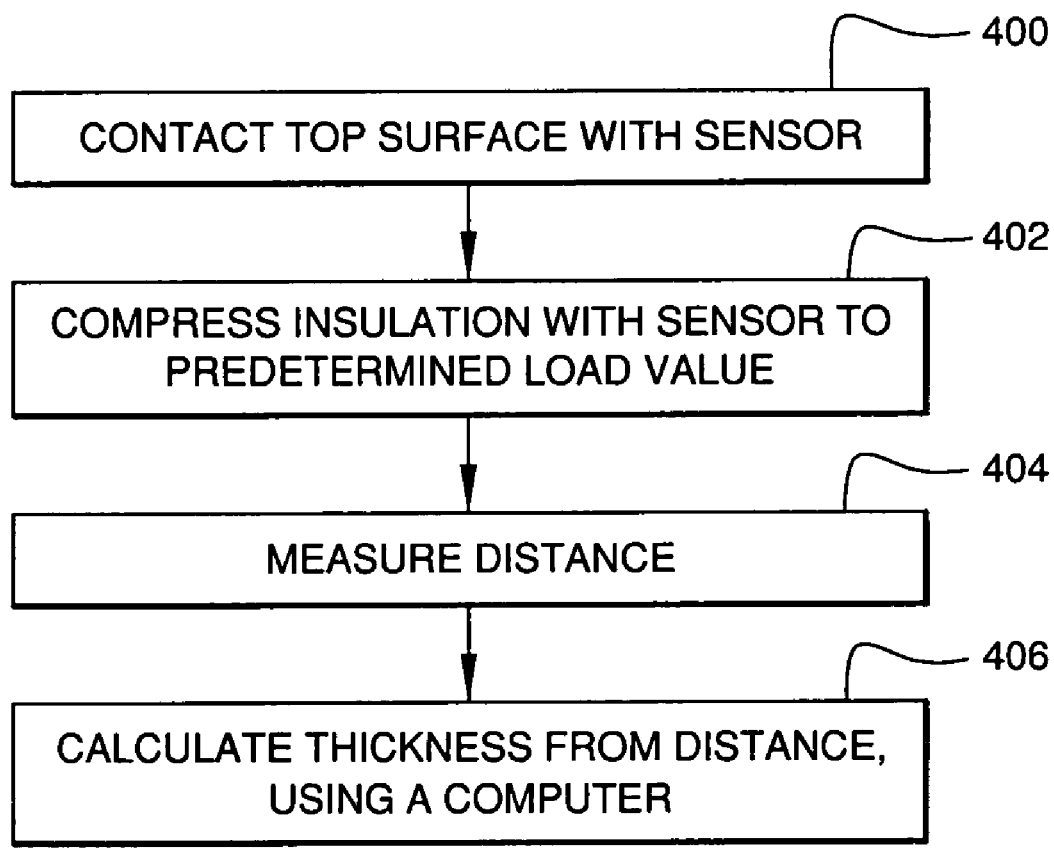
FIG. 4 is a flow chart diagram of an exemplary method.
Figure 5:
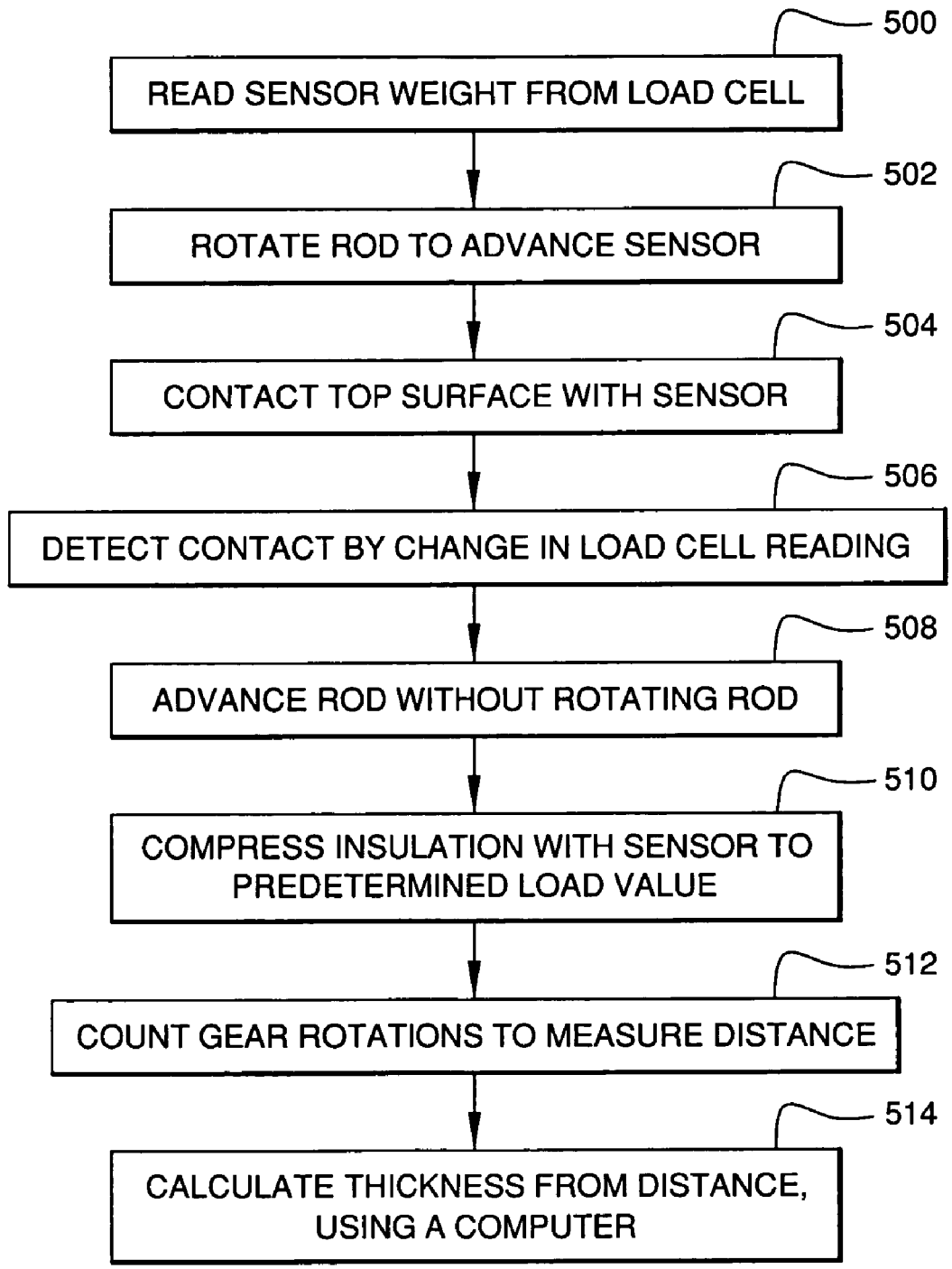
FIG. 5 is a more detailed flow chart diagram of an exemplary method according to one embodiment of the method of FIG. 4.

An assembly 110 includes a plurality of force measuring devices such as load cells 200 (FIGS. 2A and 2B). Each load cell 200 can be used to take an independent measurement indicative of insulation thickness at a different location on the insulation 132. For example, as shown in FIG. 3, a rectangular array of contacting devices or sensors 121 may be provided, with each sensor coupled to a respective load cell 200 (FIG. 2) in a manner described below. Although FIG. 3 shows 15 sensors, any desired number of sensors may be included. The load cells 200 may be of a conventional type, capable of producing an electrical signal that varies as a function of a force applied to a member of the load cell. Preferably the load cell output signal is substantially linear in the relevant deflection range, but a load cell with a small non-linearity may be used, so long as the response of the load cell is accurate and reliable. The load cell 200 includes at least one elastic member 201 (shown in FIG. 2B) that deflects in a predictable manner in response to an applied load, and at least one transducer (e.g., at least one strain gage, not shown) attached to the elastic member 201, for transmitting an electrical signal representative of the deflection of the elastic member. In some embodiments, each load cell 200 is connected by a wired link to a terminal at the port 150, for connection to the computer processor 160. In other embodiments, the load cells may be connected to the computer by way of wireless links. As shown in FIG. 2B, at least one of the gears 210 is coupled to a counter 230 that counts rotation of the gear. Although not shown, the counter 230 may be slidably mounted on a guide that allows substantially frictionless up-and-down translation of the counter 230 and its attached gear(s) 210.

Reference is again made to FIGS. 1, 2A and 2B. A plurality of sensors 120 are provided. Each sensor 120 includes a disk 121 and a rod 122 from which the disk 121 is suspended. Each rod 122 is mechanically coupled to a load measuring device, such as one of the load cells 200 described above. Each rod 122 has a means for measuring displacement of the rod. For example, in some embodiments, at least a portion of each rod 122 has threads 124, and each load cell 200 has a pair of gears 210 that engage the threads 124.

Each pair of gears 210 is coupled to its respective load cell 200 in a manner that can transmit a force from the gears 210 to the load cell 200, while allowing the gears to be translated towards or away from the load cell. For example, in some embodiments, the gears 210 are coupled to the load cell 200 by one or more spring members 220. The tension in the springs 220 is transmitted from the gears to the load cell. The load cell 200 has at least one member 201 that is deflected by the tension in the springs 220, with a transducer mounted thereon to provide a measure of the tension in the springs. The springs 220 allow the displacement of the gears 210 to be a multiple (real number greater than one) of the deflection of the load cell member. Load cell members are extremely sensitive and usually measure relatively small deflections. The springs 220, on the other hand, can be selected to elongate by a substantially greater distance (e.g., about one centimeter to about five centimeters).

The spring 220 should accommodate an elongation that is at least as large as the elongation due to the weight of the sensor assembly 120, plus the anticipated distance of the compression of the insulation material during use. For example, assuming a nominal insulation thickness of about 18 cm (7 inches), if the desired compression is about 10% of the insulation thickness, then the spring should be sized to extend elastically by at least about 1.8 cm (0.7 inch) to accommodate compression. The additional elongation to be accommodated based on the weight of the sensor assembly is readily calculated by Hooke's law: $x=-W/k$, where x is the additional elongation, W is the weight of the spring, and k is the spring constant.

Each rod 122 can be moved in two different modes. In the first mode, the rod 122 is rotated without rotating the gears 210, so that the rod advances relative to the gears by virtue of the gear-teeth engagement. The first mode is used to advance the sensor 120 towards the insulation without registering a change in compression of the insulation 132. While the rod 122 is being rotated in the first mode to advance the sensor 120 towards the insulation 132, but before the disk 121 contacts the insulation, the force exerted on the load cell reflects the weight of the sensor assembly 120. Although transient changes in the sensor signal may be observed during motion of the sensor 120, when these transient changes settle out, the observed weight remains constant before the disk 121 contacts the insulation. The reading of the load cell can be zeroed to compensate for the weight of the sensor 120 itself. If the load cell reading is not zeroed, then differential readings are used to compensate for the weight of the sensor 120.

When the rod contacts the insulation the observed force on the load cell begins to decrease as insulation pushes the disk upwards. At this point, the rod can be moved in the second mode.

In the second mode, the rod 122 is advanced (translated) without rotating the rod 122, so that the gears 210 are rotated by virtue of the gear-teeth engagement. The second mode is used to detect a change in compression after the sensor 120 contacts the insulation 132. At least one of the gears 210 is coupled to a counter 230 (shown in FIG. 2B) that is capable of counting the number of rotations of the gear when the rod 122 is translated relative to the gears. 210 without rotating the rod. There is a direct proportional relationship between the number of rotations of the gears and the displacement of the rod 122. This ratio is determined solely by the geometry of the gears and the threads of the rod.

The sensor 120 is translated downward until a predetermined force is measured by the load cell 200, that is, until a particular signal value is output by the load cell 200, corresponding to a predetermined compressive stress. The count of gear rotations corresponding to this predetermined force is determined by the output of the counter. If the load cell signal is not zeroed to compensate for the sensor weight, then $\sigma=(W-F)/A$, where F is the force measured by the load cell (a predetermined constant), and W is the weight of the sensor 120, (a constant), and A is the area of the disk 121 (also a constant). That is, the compression stress equals (the difference between the weight of the sensor 120 and the compression force on the insulation) divided by the area of the disk 121. Therefore, given a predetermined load cell signal, a is also a predetermined constant. In either case, given a predetermined force (or load cell output value) and a predetermined disk area, a corresponding value of $\sigma$ is uniquely determined, and the only dependent variable is the count of gear rotations while the rod 122 is advanced without rotating the rod, which count is directly proportional to the change in thickness.

The strain, which is given by: $\epsilon$=(change in thickness)/thickness is a function of the compression stress $\sigma$. For small values of $\epsilon$, the relationship between $\epsilon$ and $\sigma$ is substantially linear, defined by a ratio like Young's Modulus of elasticity, so that $\epsilon=(\sigma)/$(constant 1). This constant can be determined experimentally for any given insulation material. Even outside the linearly elastic region, the relationship between $\epsilon$ and $\sigma$ is predictable and can be determined experimentally, so that a table lookup can be used to determine the value of $\epsilon$ for any given $\sigma$. Once $\epsilon$ is known (assuming insulation in the linear compression region), the original thickness of the insulation can be determined as follows:

Thickness=(Change in thickness)/$\epsilon$ (1)

Given that change in thickness is proportional to the number of gear rotations during measurement,
(Change in thickness)=(constant 2)*(No. of gear rotations) (2)

Thickness=(constant 2)*(No. of gear rotations)/$\epsilon$, (3)

Since $\epsilon=(\sigma)/$(constant 1), (4)

Thickness=(No. of gear rotations)/[$(\sigma)/$(constant 3)]. (5)

where constant 3=(constant 1*constant 2)

Because the material is compressed until a reaches a known, predetermined constant, Thickness=(constant 4)*(No. of gear rotations). (6)

Thus, given any output signal 162 of the load cell 200, one can calculate $\sigma$, $\epsilon$ and the original thickness. The original thickness can then be determined from $\epsilon$ and the change in thickness. Alternatively, given the predetermined load cell output signal, sensor weight and disk area, one can directly calculate the original thickness as a function of the number of gear rotations.

Figure 6:
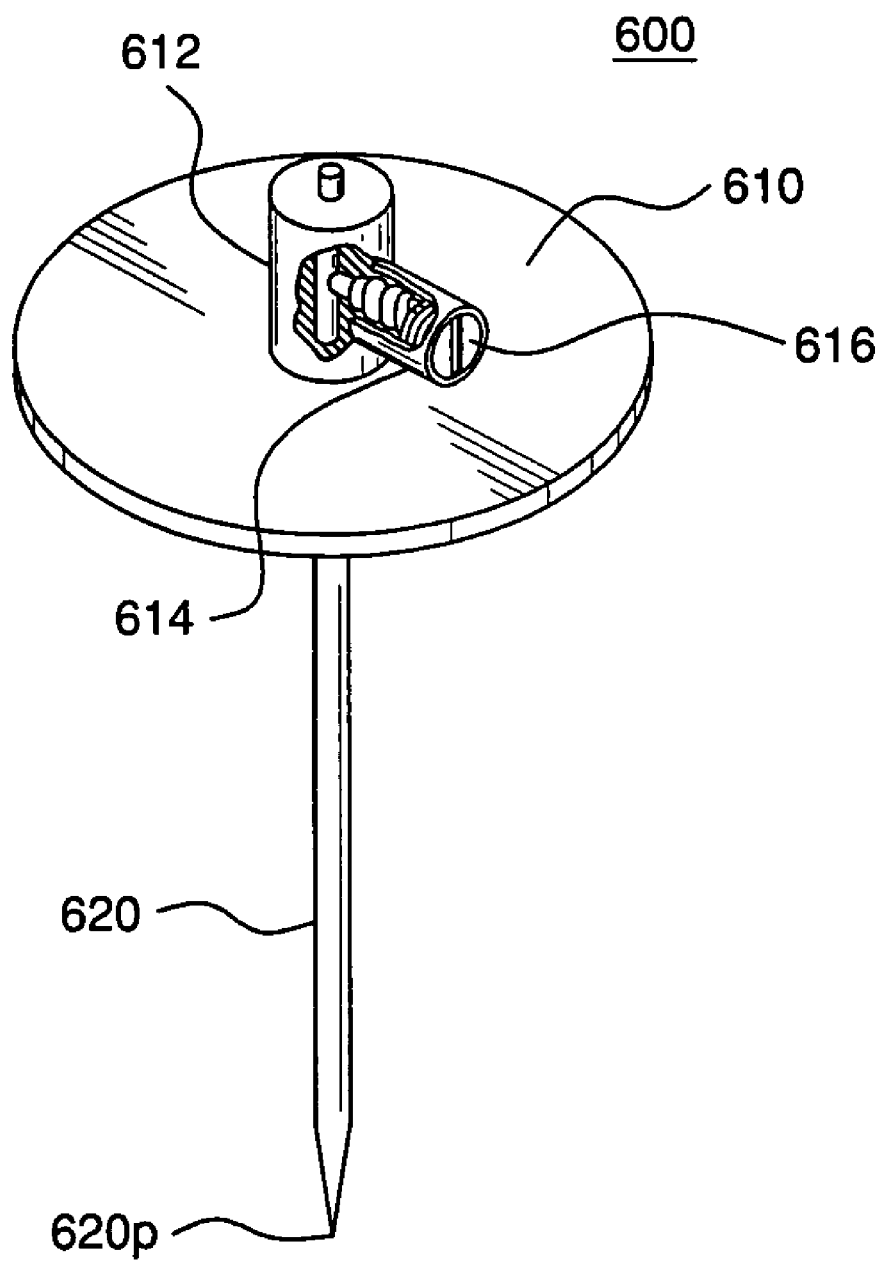
FIG. 6 is a diagram of a conventional gage for measuring insulation thickness.

Alternatively, a table can be generated listing the thickness corresponding to any given count of gear rotations (given a predetermined disk area and load cell output signal). Then, upon collection of any output signal, the thickness of the insulation at the measured location can be determined by a table look up without performing additional calculations. To maintain compatibility with ASTM C167 ("Standard Test Methods for Thickness and Density of Blanket or Batt Thermal Insulation"), which is incorporated by reference herein, sample compressions that follow ASTM C167 can be predetermined and stored in the table. That is, the ASTM C167 apparatus and method of FIG. 6 can optionally be used to calibrate the present apparatus 100.

As shown in FIG. 1, the apparatus further comprises a processor 160 connected to the at least one load cell 200, for receiving and storing the signal representing the compressive load. The processor may be a programmed general purpose computer, or a data acquisition system. The processor 160 includes means for determining the thickness of the layer of insulation based on the measured distance.

The determining means preferably includes computer program code for inputting parameter values. The parameter values can include, for example, the response profile of the load cell, the constant of proportionality between the count of rotations of the gears 210 and the translation of the rod 122, the area of the disk, the ratio of the compressive stress to compressive strain (in the linear region), or a set of polynomial coefficients describing the relationship between the compressive stress and compressive strain, or a detailed table of the relationship between the compressive stress and compressive strain.

In some embodiments, the determining means include: means for calculating a stress applied to the top surface; means for determining a strain of the layer of insulation based on a predetermined relationship between the stress and the strain of a material from which the layer of insulation is made; and means for calculating the thickness of the layer of insulation from the strain and the measured distance.

In some embodiments, the determining means include a program employing a linear or polynomial equation to calculate the thickness as a function of the number of rotations of gears 210 during while the rod 122 is advanced without rotating the rod. An example of a linear equation is described above. If the relationship between the applied stress and the strain for the blanket material displays any non-linearity, a polynomial equation can readily be developed based on calibration data.

In some embodiments, the calculating means include a program employing a table look up to determine the thickness as a function of the number of rotations of gears 210 during while the rod 122 is advanced without rotating the rod.

OPERATION

If the sample being measured is a continuous blanket or batt, the length and width of the sample are measured to make sure that the sample fits into the brackets 140, to avoid sideways compression of the insulation material.

Using the computer program code on the computer 160, the user enters the predetermined compression load of the sample. This may be entered in terms of a raw sensor output value, or a compression stress value, from which the computer 160 can derive the corresponding sensor value. This tells the computer when to begin to record the counter value indicating the distance through which the sample is compressed. A plurality of predetermined load values may be entered, corresponding to a plurality of data points to be collected by each sensor 120. If the thickness is calculated from the response of the sensor using a linear or polynomial equation, the collection of multiple points for each sensor can confirm the accuracy of the model coefficients. A final predetermined compression load is also input, from which the processor determines when to stop collecting data.

If the apparatus includes multiple sensors 120 and load cells 200, then the processor 160 may allow the user to selectively activate or de-activate individual load cells. If a sample 132 is used having a smaller length or width than that which can be accommodated by the brackets 140, then any load cells 200 corresponding to sensors that lie outside of the perimeter of the sample can be de-activated.

Each of the active load cells 200 measures an individual sample compression characteristic at a respective location on the sample, from which a respective thickness value is determined by calculation or table look up. The average thickness of the sample can be determined as an average of the individual thickness values.

Although the examples described above use a fixed predetermined compression load (stress), and the distance of travel by the sensor is measured as the dependent variable, in other embodiments, the sensor may be moved a predetermined distance and the corresponding compression load measured. Given the known relationship between the stress and strain as described above, there is still only one dependent variable (the original thickness), which can be readily calculated. To ensure that the insulation is not subjected to an excessive compressive load, the predetermined distance can be selected to be not more than about 5% to about 10% of a thickness that is on the low end of the range of thicknesses to be measured.

Figure 7:
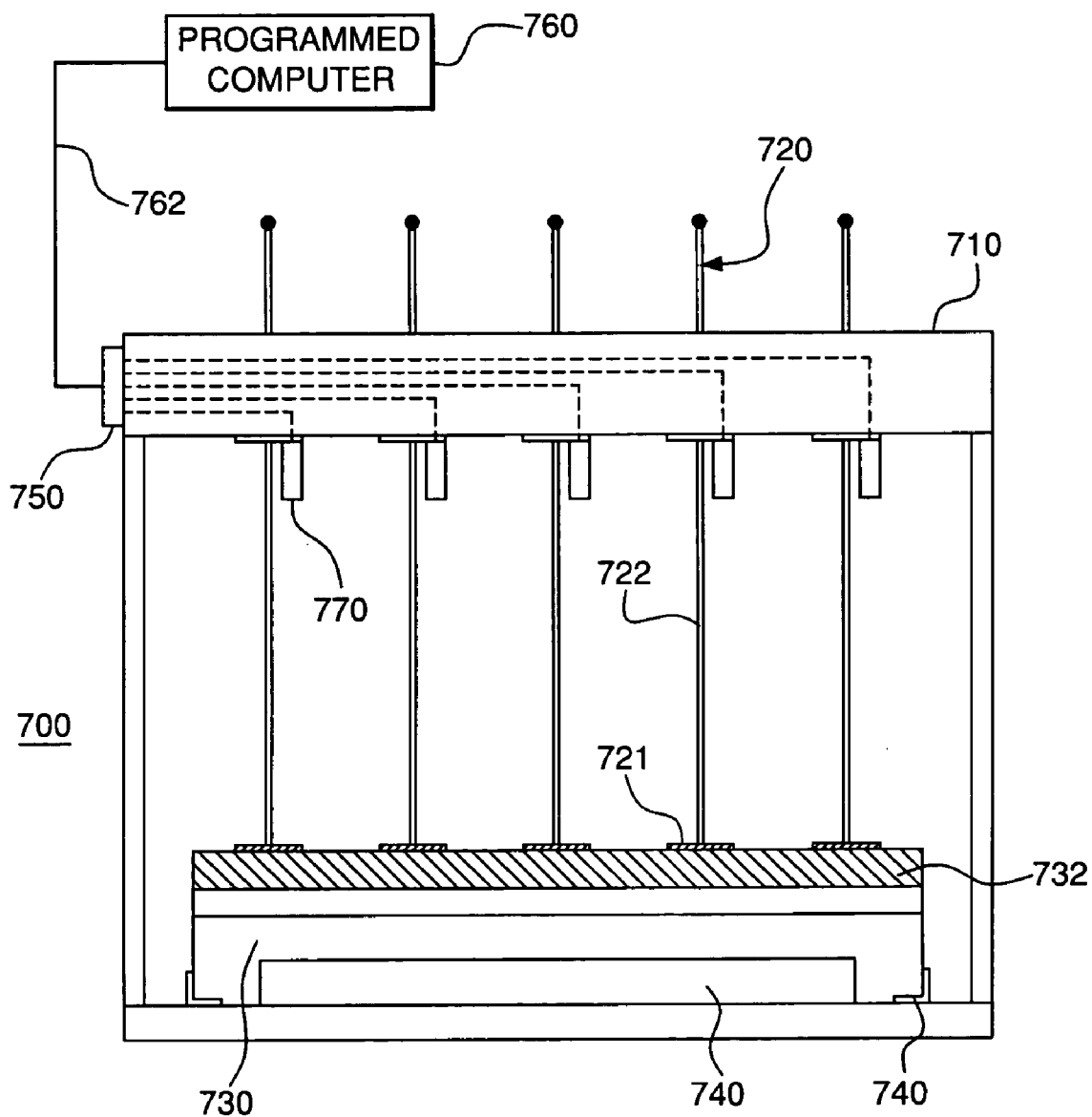
FIG. 7 is a schematic diagram of an exemplary apparatus according to another embodiment of the invention.

Although the example described above uses a load cell and a threaded rod engaging gears coupled to a counter to determine the distance through which the insulation is compressed, other distance measuring means may be used. For example, instead of gears, a counter and a threaded rod, the sensor 720 may be sensed by an interferometer, such as a micro laser interferometer 770 (shown in FIG. 7) by (Canon, Inc. of Tokyo, Japan) to measure the distance the sensor 721 moves while compressing the insulation 732. An interferometer 770 offers a more accurate and precise distance measurement. The interferometer 770 could measure the distance from a fixed reference surface to the disk 721 at the time when contact is detected and at the time the desired compression is achieved. In alternative embodiments, not shown, the interferometer can be positioned on the disk 721 and measure the distance to the fixed reference surface above (while taking the interferometer weight into account in measuring the force on the disk 721). Other elements of FIG. 7 that correspond to elements of FIG. 1 are indicated by having the same last two significant digits, including apparatus 700, load cell assembly 710, sensor assembly 720, disk 721, rod 722, box 730, brackets 740, connector 750, computer 760, signals 762. In the embodiment of FIG. 7, the load cell assembly does not require gears or counters, and the rods 722 do not require the threads. Each rod 722 is coupled to a respective load cell, for example by a respective spring. The other elements can be the same as shown in FIG. 1. In an interferometer embodiment, the compression force can be measured by a load cell in the same manner as described above. Two interferometer readings are taken, one reading at the point where the load cell first senses a compression load (i.e., when the sensor 721 contacts the insulation), and the second reading when the predetermined compressive load is reached. The difference between the two indicates the change in thickness.

Some elements in embodiments of the present invention may be implemented in the form of computer-implemented processes and apparatus for practicing those processes. These elements of the present invention may also be embodied in the form of computer program code embodied in tangible media, such as floppy diskettes, read only memories (ROMs), CD-ROMs, hard drives, "ZIP™" high density disk drives, flash memory drives, or any other computer-readable storage medium, wherein, when the computer program code is loaded into and executed by a computer, the computer becomes an apparatus for practicing the invention. The present invention may also be embodied in the form of computer program code, for example, whether stored in a storage medium, loaded into and/or executed by a computer, or transmitted over some transmission medium, such as over the electrical wiring or cabling, through fiber optics, or via electromagnetic radiation, wherein, when the computer program code is loaded into and executed by a computer, the computer becomes an apparatus for practicing the invention. When implemented on a general-purpose processor, the computer program code segments configure the processor to create specific logic circuits.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for determining a thickness of a layer of insulation, comprising the steps of:
   contacting a top surface of a portion of the layer of insulation;
   compressing the portion of the layer of insulation until a predetermined compressive load is achieved, including physically moving the top surface at a location in the portion of the layer of insulation, wherein the predetermined compressive load corresponds to a strain of about 10% or less in the thickness;
   measuring a distance through which the top surface is moved during the compressing step; and
   calculating the thickness of the layer of insulation electronically in a programmed computer processor, based on the measured distance.

2. The method of claim 1, wherein the predetermined compressive load corresponds to a strain of about 5% or less in the thickness.

3. The method of claim 1, wherein the contacting step includes contacting the top surface with a sensor that is used to perform the compressing step.

4. The method of claim 3, wherein the sensor is attached to a load cell.

5. The method of claim 1, wherein the calculating step includes:
   calculating a stress applied to the top surface;
   determining a strain of the layer of insulation based on a predetermined relationship between the stress and the strain of a material from which the layer of insulation is made; and
   calculating the thickness of the layer of insulation from the strain and the measured distance.

6. A method for determining a thickness of a layer of insulation, comprising the steps of:
   contacting a top surface of a portion of the layer of insulation with a sensor that is used to perform the compressing step, wherein the sensor is attached to a load cell;
   compressing the portion of the layer of insulation until a predetermined compressive load is achieved, including physically moving the top surface at a location in the portion of the layer of insulation, wherein the load cell initially outputs a signal corresponding to a weight of the sensor, and the contacting is detected when the signal output by the load cell begins to change;
   measuring a distance through which the top surface is moved during the compressing step; and calculating the thickness of the layer of insulation electronically in a programmed computer processor, based on the measured distance.

7. The method of claim 6, wherein the sensor is coupled to the load cell by a threaded rod and a gear arrangement, and the method further comprises:
   rotating the threaded rod to advance the sensor before the contacting step; and
   advancing the sensor without rotating the rod after the contacting step.

8. The method of claim 7, wherein the measuring step includes determining the distance the threaded rod is advanced after it comes in contact with the insulation by counting a number of rotations of the gear arrangement while advancing the sensor without rotating the rod.

9. The apparatus of claim 6, wherein the sensor includes a disk and a rod from which the disk is suspended, the rod being mechanically coupled to the load cell.

10. An apparatus comprising:
   at least one sensor for contacting a top surface of a portion of a layer of insulation and compressing the portion of the layer of insulation, wherein the sensor includes a disk and a rod from which the disk is suspended, the rod being mechanically coupled to the load cell, at least a portion of the rod has threads, and the load cell has gears that engage the threads;
   at least one load cell coupled to the sensor for measuring a compressive load due to compression of the portion of the layer of insulation by the sensor and outputting a signal representing the compressive load; and
   means for measuring a distance through which the sensor is moved during compression of the portion of the layer of insulation by the sensor.

11. The apparatus of claim 10, wherein the gears engage the threaded rod, so that the gears rotate if the rod is translated without rotating the rod.

12. The apparatus of claim 10, wherein the gears are coupled to the load cell by springs.

13. The apparatus of claim 10, further comprising a processor connected to the at least one load cell, for receiving and storing the signal representing the compressive load.

14. An apparatus comprising:
   at least one sensor for contacting a top surface of a portion of a layer of insulation and compressing the portion of the layer of insulation;
   at least one load cell coupled to the sensor for measuring a compressive load due to compression of the portion of the layer of insulation by the sensor and outputting a signal representing the compressive load; and
   means for measuring a distance through which the sensor is moved during compression of the portion of the layer of insulation by the sensor; and
   a processor connected to the at least one load cell, for receiving and storing the signal representing the compressive load, wherein the processor includes means for calculating the thickness of the layer of insulation based on the measured distance, wherein the calculating means include:
      means for calculating a stress applied to the top surface;
      means for determining a strain of the layer of insulation based on a predetermined relationship between the stress and the strain of a material from which the layer of insulation is made; and
      means for calculating the thickness of the layer of insulation from the strain and the measured distance.

15. The apparatus of claim 14, wherein the measuring means include at least one interferometer.

* * * * *